US012750584B2

(12) United States Patent
Geissler et al.

(10) Patent No.: US 12,750,584 B2
(45) Date of Patent: Sep. 29, 2026

(54) MEDICAL VISUALISATION SYSTEM AND METHOD FOR VIDEO STABILISATION IN SUCH A SYSTEM

(71) Applicant: CARL ZEISS MEDITEC AG, Jena (DE)

(72) Inventors: Enrico Geissler, Jena (DE); Philipp Brenner, Karlsruhe (DE); Dominik Scherer, Aalen (DE); Matthias Hillenbrand, Jena (DE); Joachim Steffen, Westhausen (DE); Christian Wolf, Aalen (DE); Bernd Krolla, Kaiserslautern (DE)

(73) Assignee: CARL ZEISS MEDITEC AG, Jena (DE)

( * ) Notice: Subject to any disclaimer, the term of this patent is extended or adjusted under 35 U.S.C. 154(b) by 155 days.

(21) Appl. No.: 18/693,568

(22) PCT Filed: Oct. 13, 2022

(86) PCT No.: PCT/EP2022/078492
§ 371 (c)(1),
(2) Date: Mar. 20, 2024

(87) PCT Pub. No.: WO2023/062121
PCT Pub. Date: Apr. 20, 2023

(65) Prior Publication Data

US 2024/0388800 A1 Nov. 21, 2024

(30) Foreign Application Priority Data

Oct. 14, 2021 (DE) ..................... 10 2021 126 658.0

(51) Int. Cl.
*H04N 23/68* (2023.01)
*A61B 90/20* (2016.01)
(Continued)

(52) U.S. Cl.
CPC ......... *H04N 23/6811* (2023.01); *A61B 90/20* (2016.02); *G02B 21/0012* (2013.01);
(Continued)

(58) Field of Classification Search
CPC .. H04N 23/6811; H04N 23/69; H04N 23/682; H04N 23/6812; A61B 90/20; G02B 21/0012; G02B 21/365
See application file for complete search history.

(56) References Cited

U.S. PATENT DOCUMENTS 8,228,390 B2 7/2012 Okada et al.
8,749,648 B1 6/2014 Kohn et al.
(Continued)

FOREIGN PATENT DOCUMENTS

CN 113132612 A 7/2021
EP 3437547 A1 2/2019
(Continued)

OTHER PUBLICATIONS

International Search Report for Application No. PCT/EP2022/078492, mailed Feb. 8, 2023 (12 pages).
Written Opinion for Application No. PCT/EP2022/078492, mailed Feb. 8, 2023 (16 pages).

*Primary Examiner* — James T Boylan
(74) *Attorney, Agent, or Firm* — NIXON PEABODY LLP; Jeffrey L. Costellia

(57) ABSTRACT

A method for video stabilisation having the following steps: a) providing a surgical microscope, comprising an image sensor, and a movement detection device which detects a movement of the image sensor and generates corresponding sensor movement data; b) detecting an object field and generating video data of the object field by means of the image sensor and generating image movement data by evaluating the video data; and c) correcting the video data, comprising c1) calculating displacement vector data which
(Continued)

only or predominantly indicate a movement of the image sensor but do not or only subordinately indicate a movement within the object field, using the combined use of the sensor movement data, wherein the image movement data which indicate changes in movement of the object field are weighted and/or filtered on the basis of the sensor movement data, and c2) correcting the video data by means of the displacement vector data.

14 Claims, 4 Drawing Sheets

(51) Int. Cl.

*G02B 21/00* (2006.01)
*G02B 21/36* (2006.01)
*H04N 23/69* (2023.01)

(52) U.S. Cl.

CPC ......... *G02B 21/365* (2013.01); *H04N 23/682* (2023.01); *H04N 23/69* (2023.01); *H04N 23/6812* (2023.01)

(56) References Cited

U.S. PATENT DOCUMENTS

| | | | | |
|---|---|---|---|---|
| 2010/0118156 | A1* | 5/2010 | Saito | H04N 5/144 348/208.6 |
| 2011/0007175 | A1 | 1/2011 | Fujita et al. | |
| 2018/0172971 | A1 | 6/2018 | Zhou | |
| 2019/0034400 | A1 | 1/2019 | Alda | |
| 2019/0107699 | A1* | 4/2019 | Iida | A61B 1/00042 |
| 2019/0394400 | A1 | 12/2019 | Tamura | |
| 2020/0412954 | A1* | 12/2020 | Gaizman | H04N 23/6812 |
| 2021/0006721 | A1* | 1/2021 | Yasuda | H04N 23/6815 |
| 2023/0144310 | A1* | 5/2023 | Konishi | G06T 7/215 348/208.4 |
| 2024/0296569 | A1* | 9/2024 | Kato | G06T 7/215 |

FOREIGN PATENT DOCUMENTS

| | | | |
|---|---|---|---|
| JP | 4274233 | B2 | 6/2009 |
| JP | 2009147727 | A | 7/2009 |

* cited by examiner

MEDICAL VISUALISATION SYSTEM AND METHOD FOR VIDEO STABILISATION IN SUCH A SYSTEM

CROSS-REFERENCE TO RELATED APPLICATIONS

The present application is the U.S. National Stage entry of International Application No. PCT/EP2022/078492, filed Oct. 13, 2022, which claims priority under 35 U.S.C. § 119 to German Patent Application No. 10 2021 126 658.0, filed Oct. 14, 2021, the contents of which are incorporated by reference herein in their entirety.

The invention relates to a medical visualization system, in particular a surgical microscope system, and to a method for video stabilization in such a system.

In medical visualization systems, e.g. in microscopy and especially in surgical microscopes, a stable live video image on a display unit (e.g. a monitor, mixed reality glasses, a digital eyepiece, a projector, etc.) is required.

It is known in this regard from EP 3437547 A1 to carry out electronic image stabilization, wherein either an image evaluation or an acceleration sensor is used as a movement detecting device in order to detect movements of the surgical microscope and the required stabilization need therefrom.

US 2018/0172971 A1 likewise uses an acceleration sensor as a movement detecting device to detect whether the image needs to be stabilized. It then performs mechanical image stabilization by way of a corresponding movement of an optical head of the surgical microscope. It is intended to distinguish different movements and in particular to carry out vibration detection based on the signals of the acceleration sensor. A frequency analysis is used to distinguish different vibration patterns, such as vibrations caused by building vibrations and vibrations caused by shocks to the surgical microscope.

US 2019/0394400 A1, which is taken into account in the preamble of the independent claims, likewise relates to image stabilization and for this purpose arranges a vibration sensor as a movement detecting device in the surgical microscope. The type of vibration is determined from its signals and the need for stabilization is determined. The image stabilization is then carried out as electronic image stabilization, i.e. by suitable processing of the video image data, or as mechanical image stabilization, i.e. by suitable displacement of optical elements or an image sensor.

CN 1 13 132 612 A describes an image stabilization method that uses different stabilization methods for different image regions, in that case foreground and background, to compensate for camera shake by means of image processing. In addition to image movement data, gyroscope data from the camera is also evaluated.

U.S. Pat. No. 8,749,648 B1 discloses, among other things, a method in which movement data which are obtained from a movement sensor and were registered during recording are used in a downstream image processing operation to stabilize the video.

In surgical microscopy, a live image is used by a physician. Time delays are extremely bothersome. The state-of-the-art technology proves to be problematic in this respect, since image stabilization is relatively computationally intensive and can therefore lead to time delays in the display of the live video. In addition, the state of the art makes it difficult to distinguish object movements from microscope vibrations.

The invention is therefore based on the object of providing improved image stabilization for surgical microscopy, which avoids the problems of the state of the art.

The invention is defined in claims 1 and 9. It provides a medical visualization system and a method for video stabilization in a medical visualization system. The medical visualization system comprises an image sensor. Furthermore, a movement detecting device is used which detects movements of the image sensor and generates corresponding sensor movement data, while simultaneously a video image of an object is generated with the medical visualization system.

As far as reference is made to a surgical microscope (system) below, this is an example of a medical visualization system.

Provision is made of a method for video stabilization in a medical visualization system comprising an image sensor, wherein the method includes the following steps:

a) providing the medical visualization system and a movement detecting device that detects a movement of the image sensor and generates corresponding sensor movement data,
b) capturing an object field and generating video data of the object field by means of the image sensor and generating image movement data by evaluating the video data, and
c) correcting the video data, comprising
    c1) calculating displacement vector data that only or predominantly reproduce a movement of the image sensor, but do not, or only to a minor degree, reproduce a movement within the object field, with the combined use of the sensor movement data and the image movement data, wherein the image movement data which reproduce movement changes in the object field are weighted and/or filtered on the basis of the sensor movement data, and
    c2) correcting the video data by means of the displacement vector data.

Provision is further made of a medical visualization system comprising an image sensor for generating video data for an object, and a movement detecting device, which detects a movement of the image sensor and generates corresponding sensor movement data, a control device comprising a processor and a memory which is connected to the image sensor and the movement detecting device via a data link, a display for displaying the video data, wherein the control device is configured to calculate displacement vector data that only or predominantly reproduce a movement of the image sensor, but do not, or only to a minor degree, reproduce a movement within the object field, with the combined use of the sensor movement data and the image movement data, wherein the image movement data which reproduce movement changes in the object field are weighted and/or filtered on the basis of the sensor movement data, and correct the video data by means of the displacement vector data and transmitting them to the display.

The invention uses the finding that a plurality of movements can occur simultaneously for image stabilization. There may be movement of the microscope relative to the object. This would be a microscope vibration, for example. However, there may also be movements of the object that occur either throughout or partially in the image. One example in surgical microscopy would be blood vessels that perform a rhythmic movement with the heart action. There may also be externally moved elements in the object that usually appear in the foreground and thus may also appear blurred. In the case of surgical microscopy, this may involve, for example, the movement of surgical instruments or tools. These different components form a movement vector and cannot be distinguished from one another by image analysis-this is true even if an acceleration sensor according to the state of the art is to be additionally used in order to detect the need for image stabilization.

The term "movement vector" refers here to a vector that reproduces all the movements in the video data, regardless of whether they are caused by the movement of the microscope relative to the object, by movements of the object itself or by movements in the foreground of the image. It can be determined from the image movement data. The "displacement vector data," on the other hand, are the displacement data obtained after the corresponding combined evaluation of image movement data and sensor movement data, and are caused exclusively or to a proportion of at least 60%, preferably 70%, with great preference 80% and most preferably 90% by movements in the object field, i.e. the desired separated-off part from the movement vector.

The correction can be performed as a simple correction of a lateral displacement, or as more complex corrections that can be summarized by the term warp. The displacement vectors preferably form a matrix, which enables a more complex correction. In the simplest case, the mean value is used as a lateral displacement. In conjunction with the third spatial direction, a superimposed magnification change using warp is the corrective action.

The invention combines the evaluation of the image and of the movement detecting device in order to separate off from the movement vector those parts which are caused by a movement of the microscope relative to the object. The movement vector and thus the image movement data indicate displacements within the video data, i.e. it has/they have not yet been separated off per se with respect to the microscope movement of interest. With the combined use of the sensor movement data and the image movement data, it is possible to weight and/or filter the movement vector on the basis of the sensor movement data. In this way, the displacement vector data which reproduce only a movement of the image sensor but no movement in the object field are generated. The use of the movement detecting device in the combined approach thus enables a weighting or a sorting out of movement vectors and thus the separation of the part of the movement vector that reproduces the movement of the microscope itself.

The combination achieves an accuracy that goes beyond the resolution of the sensor movement data.

Moreover, this approach is not only particularly computationally efficient and associated with little time delay, it also has the additional advantage that a large variety of movement detecting devices can be used without the evaluation having to be carried out differently. The separation of the part of interest is completely independent of the type of movement detecting device. This achieves an easy adaptability or retrofitting option for existing surgical microscopes.

The movement detecting device may use one or more of the following sensors/techniques:

a. a single-axis to six-axis acceleration sensor that measures linear accelerations along three axes and is located on the image-recording unit or the object;
b. an inertial measurement unit, which measures linear accelerations, e.g. along three axes and rotations around three axes ("gyroscope") and, if applicable, also measures the magnetic field (9 DOF absolute orientation sensors) and is located on the image-recording unit or the object;
c. a wide-angle vicinity camera, which is also mounted on the image-recording unit, but which looks at a larger or different image field (possibly also in a different direction);
d. a further camera or, more generally, an external tracking system, e.g. a laser tracking system, which is not mounted on the image-recording unit and determines the movement of the image-recording unit from the outside. For this purpose, additional elements such as markers or retro-reflectors can be placed on the image-recording unit, if required;
e. a projection of markers/patterns from the image-recording unit and determination of the relative position of the markers/patterns to the image content. The markers and the remaining image content can be located either in the same or in a deliberately separable spectral range (e.g. IR);
f. a projection of markers/patterns coming from an external static object;
g. a tracking of distinctive object features with a separate tracking system, such as pupil tracking in surgical microscopes in ophthalmology, and
h. a second image sensor, as may be present in the image-recording unit of stereo microscope systems.

In surgical microscopes, the image sensor is usually attached to a stand or arm. It is then preferable to use a vibration model of the stand or arm to calculate the displacement vector data. This application is used to proceed from a typical vibration behavior of the image sensor in order to filter/weight the movement vector therefrom in order to determine the displacement vector data that can be used for the correction of the video data. The vibration model is not intended to perform an analysis of the vibrations and, in particular, to check for vibrations with specific parameters.

In embodiments, the object is imaged with a specified total magnification and displayed on a display. The ratio of optical magnification (optical zoom) to digital magnification (digital zoom) may preferably be readjusted here, if appropriate. If no vibration in the plane parallel to the image sensor around a rest position is detected, the magnification desired by the user is primarily set by the optical magnification of the system. This results in maximum image quality. If, on the other hand, a vibration parallel to the image sensor around a rest position has been detected, it is possible to in part optically zoom out and digitally zoom in. This makes available a larger region on the image sensor for the subsequent cycle, which can be used for subsequent correction steps, and the result is an optimized video stability despite the moving image-recording unit.

Defocusing may occur when there are vibrations perpendicular to the plane of the image field provided by the image sensor. Embodiments therefore preferably adjust a pupil diaphragm appropriately, because the pupil diaphragm is known to influence the depth of field of the imaging. If the pupil diaphragm is narrowed, the depth of field increases. The image brightness is then customarily kept constant by adapting an electronic gain, i.e. when the pupil diaphragm is being closed, the image gain is increased and vice versa. The result of the vibration analysis can now be taken into account when adjusting the pupil diaphragm. The diaphragm of the optical system and the electronic gain or the exposure time are then readjusted. If no vibration around a rest position perpendicular to the image field (along the optical axis) is detected, the diaphragm of the system is opened wide to obtain the best possible image quality. If, on the other hand, a vibration around a rest position perpendicular to the image field is detected, the image diaphragm may be set to a smaller value to increase the depth of field. In order to obtain a similar image brightness, the electronic gain and/or the exposure time may be adapted.

The same applies to the focal plane of the optical system. It too is affected by vibrations perpendicular to the plane of the image field, but not by vibrations in the plane of the image field. The focal plane of the optical system is readjusted. If a vibration around a rest position perpendicular to the image field (along the optical axis) is detected, the focal plane is readjusted according to a position predicted for the next exposure period and/or the depth of field is set by partially closing the diaphragm in such a way that a sufficiently large/the entire vertical vibration range is imaged with sufficient sharpness.

The described surgical microscope system or the described method also has the advantage that always only vibrations of the surgical microscope are detected. A movement of the object is no longer incorrectly transferred from the movement vector to the movement vector data, as can be the case, for example, with a pure image analysis. Furthermore, it is not necessary that, as in EP 3437547 A1, an image sensor must be used which has more pixels than the display device, which is used to display the video. In embodiments, the image sensor and display have the same number of pixels.

The described concept further achieves image stabilization in 3D, i.e. also along the optical axis. Image blurring caused by vibrations can be corrected thereby.

It is preferable to filter on the basis of the sensor movement data. For example, a movement vector range can be defined, and only image movement data that lie within this range will be used for the displacement vector data. In this case, not only a Yes/No selection is possible in the filtering, but also a weighting of the image movement data, e.g. a distance weighting. Machine learning can also be used to improve filtering.

Insofar as the invention is described here with reference to a surgical microscope, the method performed on the surgical microscope does not necessarily have to be linked to a surgical or diagnostic method. In embodiments, no therapy or diagnostic method is carried out on a living, human or animal body. Examples of such non-therapeutic and non-diagnostic uses of a surgical microscope are found in particular in ophthalmology, e.g. when viewing the ocular fundus, or in the preliminary clarification of a later operating field, e.g. in the oral cavity, in the nasopharynx or in the region of the ear. Similarly, a surgical microscope can also be used for the preparation of a transplant, i.e. on the non-living human body.

It goes without saying that the features mentioned above and the features yet to be explained hereinafter can be used not only in the specified combinations but also in other combinations or on their own, without departing from the scope of the present invention.

The invention will be explained in even greater detail below on the basis of exemplary embodiments with reference to the accompanying drawings, which likewise disclose features essential to the invention. These exemplary embodiments are provided for illustration only and should not be construed as limiting. For example, a description of an exemplary embodiment having a multiplicity of elements or components should not be construed as meaning that all of these elements or components are necessary for implementation. Rather, other exemplary embodiments may also contain alternative elements and components, fewer elements or components, or additional elements or components. Elements or components of different exemplary embodiments can be combined with one another, unless indicated otherwise. Modifications and variations that are described for one of the exemplary embodiments can also be applicable to other exemplary embodiments. In order to avoid repetition, elements that are the same or correspond to one another in different figures are denoted by the same reference signs and are not explained repeatedly. In the figures:

Figure 1:
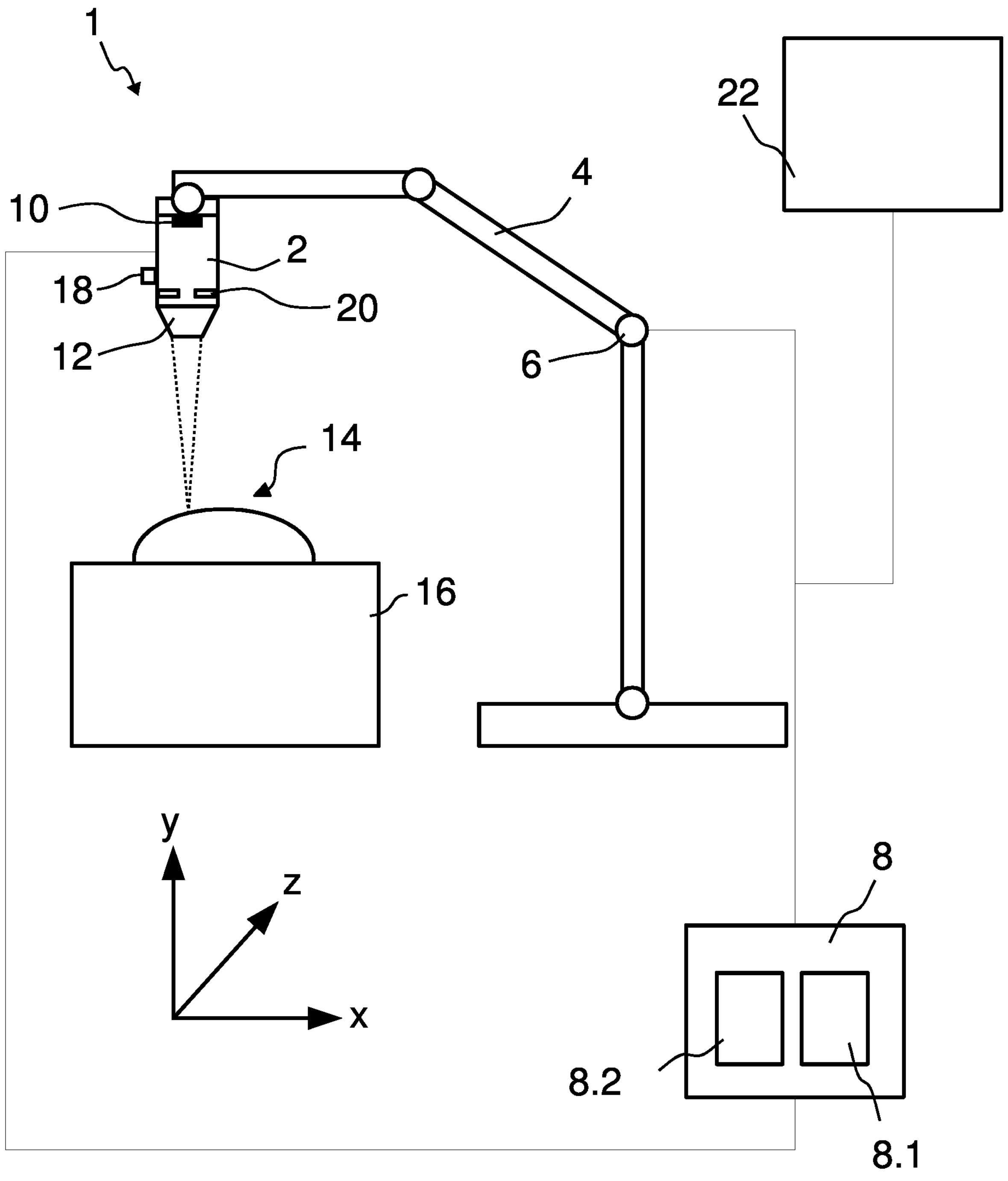
FIG. 1 shows a schematic illustration of a surgical microscope system.

FIG. 1 schematically shows a surgical microscope 1, which together with an acceleration sensor and a control device forms a surgical microscope system. The surgical microscope 1 comprises a microscope head 2, which is attached to an arm 4. The arm 4 is adjustable via joints 6 so that the position of the microscope head 2 in the 3D space can be set. The joints 6 have drives for this purpose in order to be able to adjust individual segments of the arm 4 relative to one another. Generally, six degrees of freedom of adjustment are possible in the surgical microscope 1, namely three of translation and three of rotation. The joints 6 are connected with respect to their drives to a control device 8, which adjusts the position of the arm 4 and thus of the microscope head 2. The microscope head 2 is likewise connected to the control device 8, which comprises a processor 8.1 and a memory 8.2. It controls the operation of the surgical microscope 1 and performs, as will be explained below, in particular image stabilization.

The microscope head 2 comprises an image sensor 10, on which an object 14, e.g. a part of a patient, which is located on a table 16, usually an operating table, is imaged through an objective 12, which is usually designed as a zoom lens.

In the microscope head 2, an adjustable diaphragm 20 is provided, which is configured as a pupil diaphragm and sets the amount of light which falls through the objective 12 onto the image sensor 10. Usually, the surgical microscope 1 also comprises further elements, for example an illumination source, etc. This is not shown in the schematic illustration of FIG. 1, as it is not relevant for the details to be described here.

The microscope head 2 is connected via a control line (not further specified) to the control device 8, which controls the operation of the surgical microscope 1 at the microscope head 2, in particular the recording of image data by the image sensor 10 and the position of the objective 12 and of the pupil diaphragm 20. The control device 8 further reads the acceleration sensor 18, which is rigidly connected to the image sensor 10 to measure the accelerations which occur at the image sensor 10.

Figure 2:
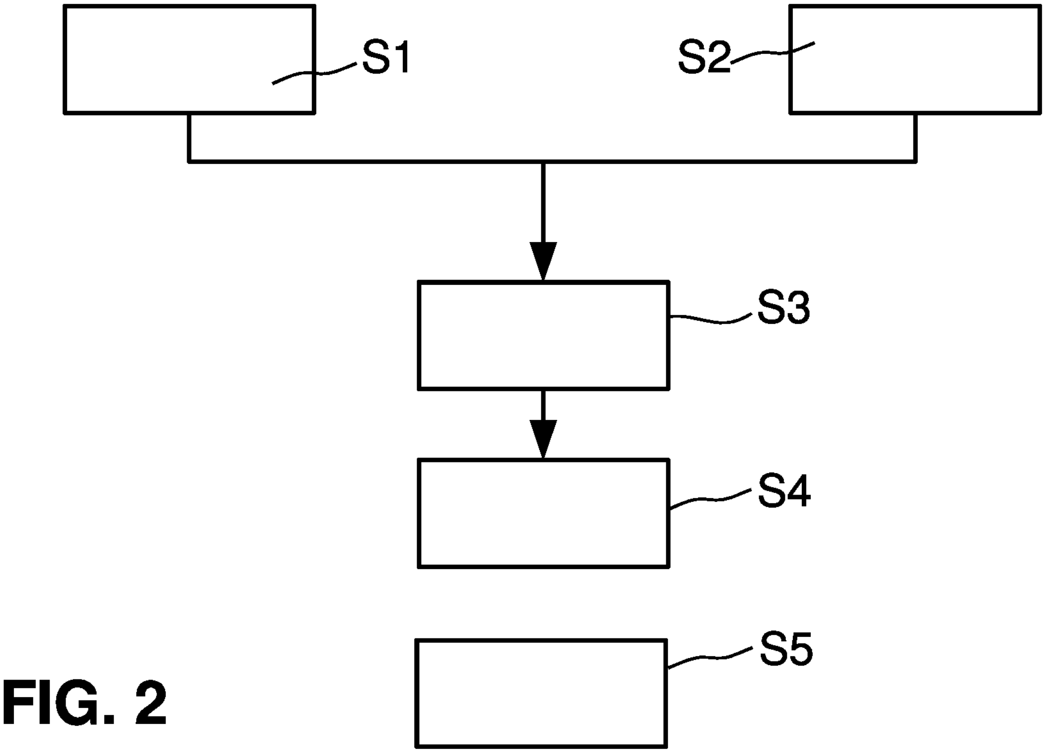
FIG. 2 shows a block diagram for a method for video stabilization.

With the aid of this surgical microscope system, video data are recorded during operation of the surgical microscope 1 and processed by the control device 8 and then displayed on a display 22. In this case, a video stabilization is carried out according to the method shown schematically in FIG. 2. In a step S1, the image information is recorded by the image sensor 10, i.e. the video data which show the object 14 are captured with a settable magnification. From the video data, image-movement data are determined by known image evaluation. The image movement data show movements in the image.

At the same time, sensor movement information is obtained in a step S2 by reading the acceleration sensor 18. In step S2, the position of the image sensor 10 is determined and the resulting sensor movement data are calculated.

Step S3 uses the combination of image movement data and sensor movement data to determine the most accurate displacement vector possible. It does not only use the pure image data from step S1 (as in EP 3 437 547 A1). Further, the evaluation of the image data is not simply made dependent on a previous classification of the sensor movement data, as would be known in the state of the art. Instead, a movement vector is first calculated based on the image movement data and then weighted and/or filtered based on the sensor movement data. In particular, based on the sensor movement data, a movement vector range is filtered in a step S4 in which image movement data may be located which are likely to originate from a movement of the microscope. Image movement data outside this range are suppressed and do not contribute to the displacement vector data.

In this context, it should be noted that the image movement data and sensor movement data can generally be regarded as movement vectors or as a movement vector group (for different pixels or partial objects). The combined aggregation of these data allows weighting and the desired differentiation of movement vectors that are not caused by the movement of the microscope. This prevents, for example, a global movement of the viewed object from being interpreted as the movement of the image-recording unit.

A further positive feature of the integration of a second piece of information (from a sensor or system information) is a reduction in the necessary computational effort and thus a reduction in the latency of the video transmission.

In step S4, for example, an algorithmic determination is made as to whether there is a vibration around a rest position with an amplitude that should be corrected for. For example, the decision made by such algorithm can be based on the following information:

a. the determined displacement vector and, if necessary, further sensor data are compared against defined threshold values using the sensor movement data;
b. the time-course of the displacement vectors and, if necessary, further sensor data from the memory element are compared with an analytical model (e.g. an exponentially decaying vibration); and
c. the profile of the displacement vectors and, if necessary, further sensor data from the memory element are examined for specific patterns by means of machine learning methods which allow a statement to be made about the presence of a vibration.

Figure 3:
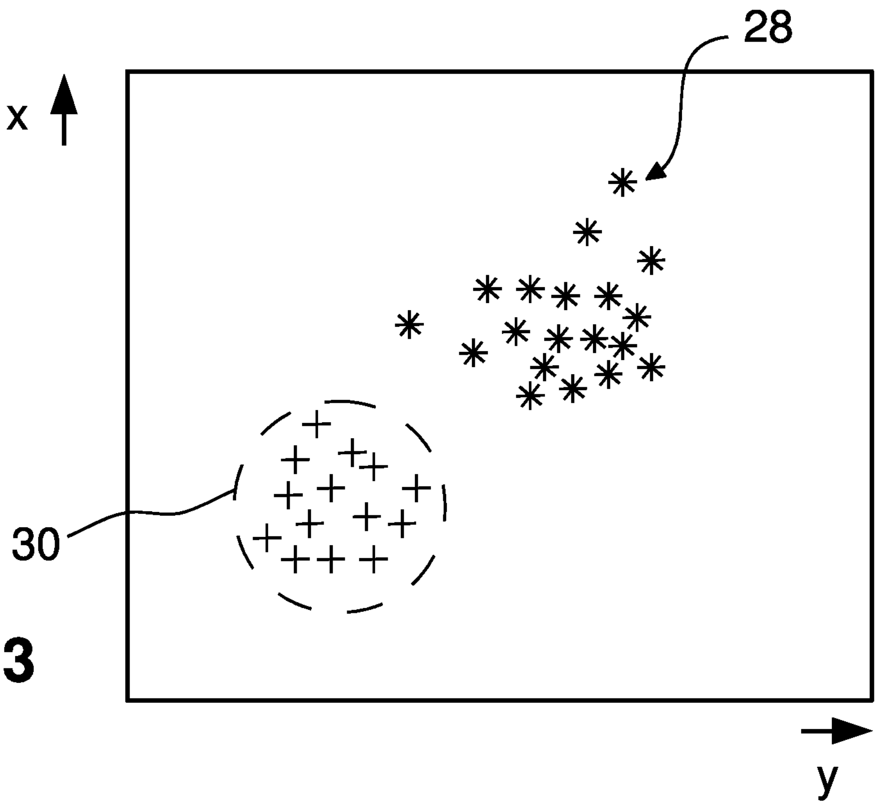
FIG. 3 shows a schematic illustration for explaining a generation of displacement vector data.

FIG. 3 shows schematically an evaluation of the movement vectors based on the sensor movement data. Movement angles are plotted on the x-axis and y-axis, and the individual measurement points are movement vectors 28, which result from the image movement data. Only movement vectors 28 (plotted with a "+") located within the region 30 are used to determine the displacement vector data. The x-and y-axes are thus the angular projections in the two-dimensional object plane. The movement vectors "+" and "*" are differentiated based on the sensor movement data.

Of course, this procedure is not limited to a two-dimensional analysis, but can also take into account the third dimension, i.e. the depth dimension of an object field. In particular, a vector length can be included as a measure of a quality of the individual movement vectors in order to obtain with highest possible precision the final displacement vector data to be determined (e.g. by averaging).

In an optional downstream step S5, the optical system of the microscope head 2 is optimized:

a. the ratio of optical magnification (optical zoom 12) to digital magnification (digital zoom) is readjusted, if appropriate. If no vibration in the plane parallel to the image sensor 10 around a rest position is detected, the magnification desired by the user is primarily set by the optical magnification of the system. This results in maximum image quality. If, on the other hand, a vibration parallel to the image sensor 10 around a rest position has been detected, it is possible to in part optically zoom out and digitally zoom in. This makes available a larger region on the image sensor 10 for the subsequent cycle, which can be used for subsequent correction steps, and the result is an optimized video stability despite the moving image-recording unit;
b. the diaphragm 20 of the optical system and the electronic gain or the exposure time are then readjusted. If no vibration around a rest position perpendicular to the image sensor 10 (along the optical axis) is detected, the diaphragm 20 of the system is opened wide to obtain the best possible image quality. If, on the other hand, a vibration around a rest position perpendicular to the image sensor 10 is detected, the diaphragm 20 may be set to a smaller value to increase the depth of field. In order to obtain a similar image brightness, the electronic gain and/or the exposure time may be adapted; and
c. the focal plane of the objective 12 is readjusted. If a vibration around a rest position perpendicular to the image sensor 10 (along the optical axis) is detected, the focal plane is readjusted according to a position predicted for the next exposure period and/or the depth of field is set by partially closing the diaphragm in such a way that a sufficiently large/the entire vertical vibration range is imaged with sufficient sharpness.

The following can be used for the sensor movement detection:

a. a single-axis to six-axis acceleration sensor that measures linear accelerations along three axes and is located on the image-recording unit or the object;
b. an inertial measurement unit, which measures linear accelerations, e.g. along three axes and rotations around three axes ("gyroscope") and, if applicable, also measures the magnetic field (9 DOF—absolute orientation sensors) and is located on the image-recording unit or the object;
c. a wide-angle vicinity camera, which is also mounted on the image-recording unit, but which looks at a larger or different image field (possibly also in a different direction);
d. a further camera or, more generally, an external tracking system, e.g. a laser tracking system, which is not mounted on the image-recording unit and determines the movement of the image-recording unit from the outside. For this purpose, additional elements such as markers or retro-reflectors can be placed on the image-recording unit, if required;
e. a projection of markers/patterns from the image-recording unit and the determination of the relative position of the markers/patterns to the image content. The markers and the remaining image content can be located either in the same or in a deliberately separable spectral range (e.g. IR);

f. a projection of markers/patterns coming from an external static object;

g. a tracking of distinctive object features with a separate tracking system, such as pupil tracking in surgical microscopes in ophthalmology, and h. a second image sensor, as may be present in the image-recording unit of stereo microscope systems.

Figure 4:
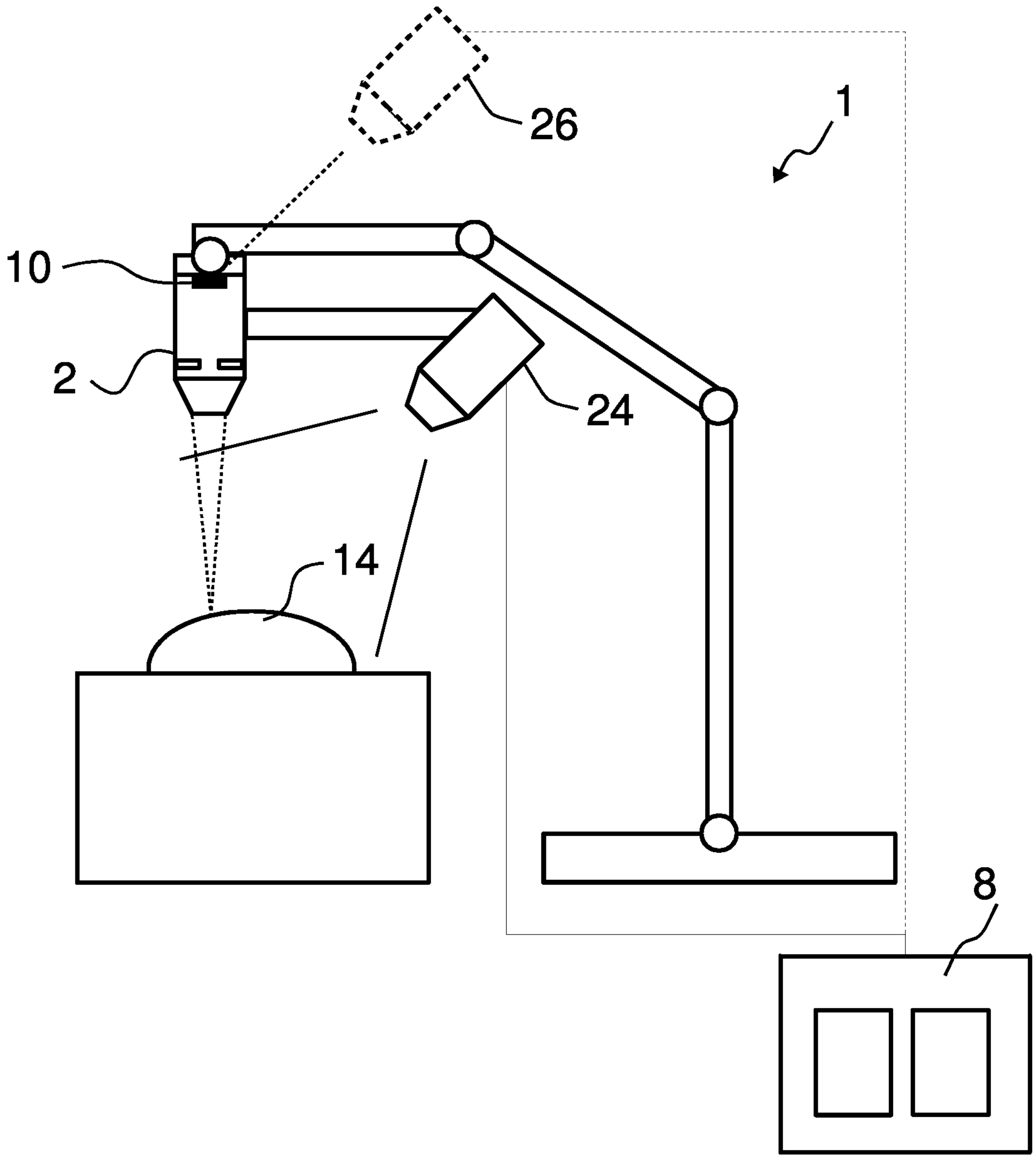
FIGS. 4 and 5 show modifications of the microscope of FIG. 1.

FIG. 4 shows by way of example the embodiment with a vicinity camera 24 or (dashed) with a tracking system 26, which captures the movement of the microscope head 2 and thus of the image sensor 10.

Figure 5:
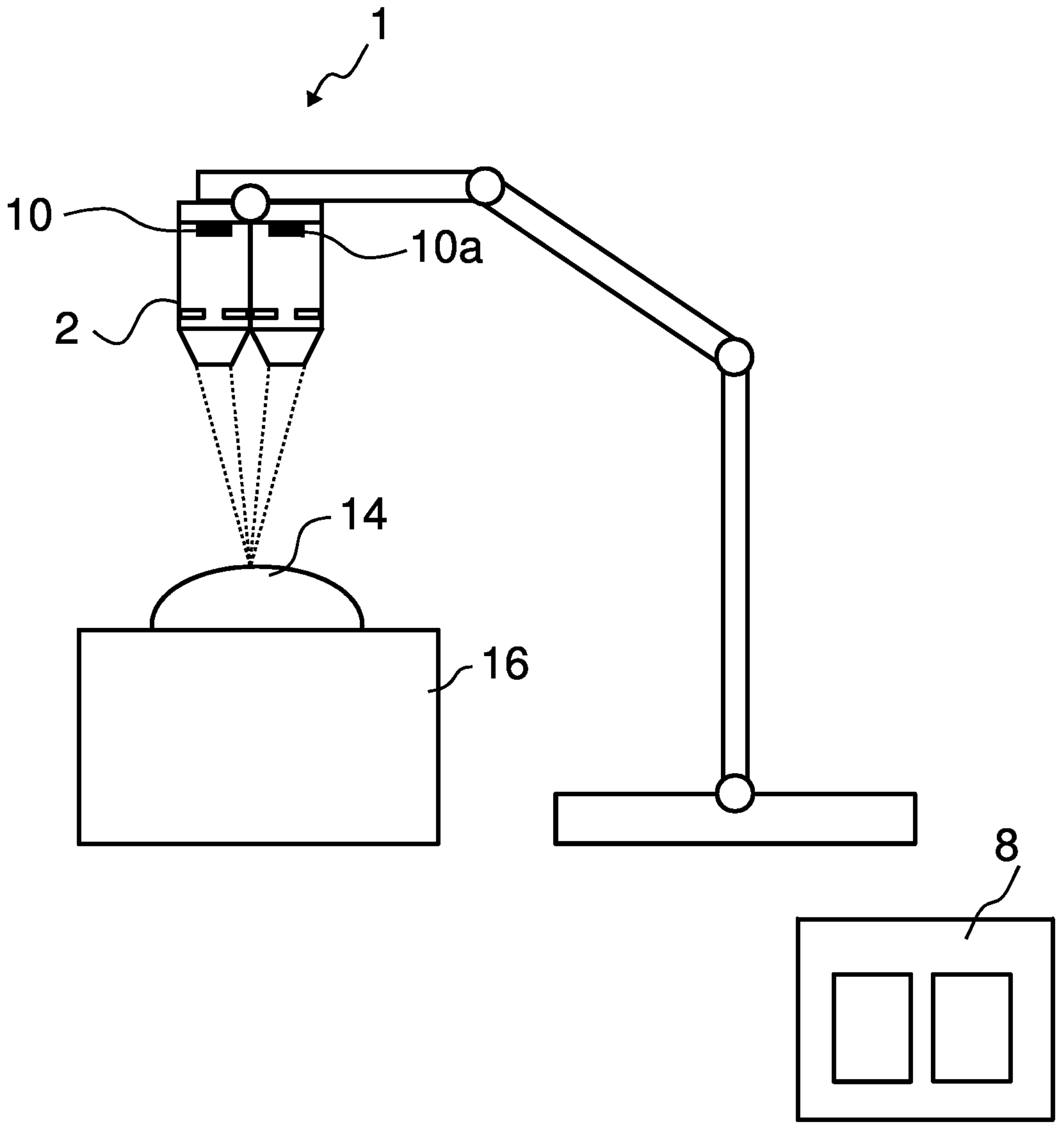

FIG. 5 shows, by way of example, the configuration of the microscope 1 as a stereo microscope, so that a second image sensor 10*a* is provided.

The method is not limited to the use on surgical microscopes, but can also be generally used in other areas in which an image-recording unit is mounted on a moving or vibrating object and a possibly moving object is viewed.

The invention claimed is:

1. A method for video stabilization in a medical visualization system, in particular a surgical microscope, comprising an image sensor, wherein the method includes the following steps:

a) providing the medical visualization system and a movement detecting device that detects a movement of the image sensor and generates corresponding sensor movement data, b) capturing an object field and generating video data of the object field by means of the image sensor and generating image movement data by evaluating the video data, and c) correcting the video data, comprising c1) calculating displacement vector data that only or to a proportion of at least 60% reproduce a movement of the image sensor, but do not, or only to a proportion of at most 40%, reproduce a movement within the object field, with the combined use of the sensor movement data and the image movement data, wherein the image movement data which reproduce movement changes in the object field are weighted and/or filtered on the basis of the sensor movement data, and c2) correcting the video data by means of the displacement vector data, wherein a movement vector range is defined on the basis of the sensor movement data and only image movement data which lie within this range are used for the calculation of the displacement vector data.

2. The method as claimed in claim 1, wherein the displacement vector data form a matrix of displacement vectors and an image distortion is corrected in step c2).

3. The method as claimed in claim 2, wherein a mean value of the displacement vectors is used for correcting a lateral displacement and, in conjunction with a third spatial direction, a superimposed magnification change is used for correction.

4. The method as claimed in claim 1, wherein the image sensor is attached to a stand or arm in the medical visualization system and a vibration model of the stand or arm is used in step c1) to calculate the displacement vector data.

5. The method as claimed in claim 1, wherein the displacement vector data are evaluated to detect whether an axial vibration running only in a plane perpendicular to the image field provided by the image sensor is present, and wherein the medical visualization system comprises an optical zoom and the object is displayed with a pre- defined total magnification, and a share of a magnification effected by the optical zoom in the total magnification is enlarged or maximized once the axial vibration has been detected.

6. The method as claimed in claim 1, wherein the displacement vector data are evaluated to detect whether a lateral vibration running parallel to the image field provided by the image sensor is present, and wherein the medical visualization system comprises an optical zoom and the object is displayed with a specified total magnification and a share of an electronic zoom in the total magnification is enlarged when the lateral vibration has been detected, and/or the medical visualization system has a pupil diaphragm upstream of the image sensor and this pupil diaphragm is enlarged or maximized in terms of the opening while adapting an electronic gain once the lateral vibration has been detected.

7. The method as claimed in claim 1, wherein the displacement vector data are evaluated to detect whether an axial vibration running only in a plane perpendicular to the image field captured by the image sensor is present, and wherein the medical visualization system comprises a pupil diaphragm upstream of the image sensor and this pupil diaphragm is decreased or minimized in terms of opening while adapting an electronic gain once the axial vibration has been detected, and/or the medical visualization system comprises a focusing device and the latter is controlled to change the focal position once the axial vibration has been detected.

8. A medical visualization system, in particular a surgical microscope system, comprising an image sensor for generating video data for an object and a movement detecting device configured to detect a movement of the image sensor and to generate corresponding sensor movement data, a control device comprising a processor and a memory which is connected to the image sensor and the movement detecting device via a data link, a display for displaying the video data, wherein the control device is configured to calculate displacement vector data that only or to a proportion of at least 60% reproduce a movement of the image sensor, but do not, or only to a proportion of at most 40%, reproduce a movement within the object field, with the combined use of the sensor movement data and the image movement data, wherein the image movement data which reproduce movement changes in the object field are weighted and/or filtered on the basis of the sensor movement data, and correct the video data by means of the displacement vector data and transmitting the video data to the display, and wherein a movement vector range is defined on the basis of the sensor movement data and only image movement data which lie within this range are used for the calculation of the displacement vector data.

9. The medical visualization system as claimed in claim 8, wherein the image sensor is attached to a stand or arm and the control device is further configured to use a vibration model of the stand or arm to calculate the displacement vector data.

10. The medical visualization system as claimed in claim 8, wherein the displacement vector data form a matrix of displacement vectors and the control device is configured to correct an image distortion.

11. The medical visualization system as claimed in claim 10, wherein the control device is configured to use a mean value of the displacement vectors for correcting a lateral displacement and, in conjunction with a third spatial direction, to use a superimposed magnification change for correction.

12. The medical visualization system as claimed in claim 8, wherein the control device is configured to evaluate the displacement vector data to detect whether an axial vibration running only in a plane perpendicular to the image field captured by the image sensor is present, and wherein the medical visualization system comprises an optical zoom, controlled by the control device, and a display, and displays the object on the display with a pre-defined total magnification, and the control device is further configured to enlarge or maximize a share of a magnification effected by the optical zoom in the total magnification once the axial vibration has been detected, and/or the medical visualization system comprises a pupil diaphragm which is arranged upstream of the image sensor and is controlled by the control device, and the control device is further configured to decrease or minimize the pupil diaphragm in terms of opening while adapting an electronic gain once the axial vibration has been detected, and/or the medical visualization system comprises a focusing device controlled by the control device, and the control device is further configured to control the focusing device for changing the focal position once the axial vibration has been detected.

13. The medical visualization system as claimed in claim 8, wherein the control device is configured to evaluate the displacement vector data to detect whether a parallel vibration running in a plane parallel to the image field captured by the image sensor is present, and wherein the medical visualization system comprises an optical zoom, controlled by the control device, and displays the object on the display with a pre-defined total magnification, and the control device is further configured to enlarge a share of an electronic zoom in the total magnification once the parallel vibration has been detected, and/or the medical visualization system comprises a pupil diaphragm which is arranged upstream of the image sensor and is controlled by the control device, and the control device is further configured to enlarge or minimize the pupil diaphragm in terms of the opening while adapting an electronic gain once the parallel vibration has been detected.

14. The medical visualization system as claimed in claim 8, wherein the movement detecting device comprises at least one of the following devices: a single-axis to six-axis acceleration sensor in a fixed location relative to the image sensor, a single-axis to six-axis inertial measurement system in a fixed location relative to the image sensor, a vicinity camera in a fixed location relative to the image sensor, a tracking system directly or indirectly monitoring the image sensor, a pattern projector in a fixed location relative to the image sensor, which projects a pattern onto the object captured by the image sensor, a tracking system directly or indirectly monitoring the object, a pupil tracker and a second image sensor that looks at the object at a stereo angle.

* * * * *